United States Patent
Lyden et al.

(10) Patent No.: US 9,357,944 B2
(45) Date of Patent: Jun. 7, 2016

(54) IMPEDANCE MEASUREMENT AND DEMODULATION USING IMPLANTABLE DEVICE

(75) Inventors: Michael J. Lyden, Shoreview, MN (US); William J. Linder, Golden Valley, MN (US); Angela M. Muttonen, Forest Lake, MN (US); George D. Ritzinger, Vadnais Heights, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1653 days.

(21) Appl. No.: 12/350,728

(22) Filed: Jan. 8, 2009

(65) Prior Publication Data
US 2009/0177110 A1    Jul. 9, 2009

Related U.S. Application Data

(60) Provisional application No. 61/010,426, filed on Jan. 8, 2008.

(51) Int. Cl.
*A61B 5/05* (2006.01)
*A61B 5/053* (2006.01)
(Continued)

(52) U.S. Cl.
CPC ............... *A61B 5/053* (2013.01); *A61B 5/029* (2013.01); *A61B 5/0538* (2013.01); *A61B 5/6846* (2013.01); *A61B 5/7203* (2013.01);
(Continued)

(58) Field of Classification Search
CPC ............ A61B 5/0031; A61B 5/04017; A61B 5/0452; A61B 5/046; A61B 5/053; A61B 5/0535; A61B 5/7203; A61N 1/3622; A61N 1/36521; A61N 1/3704; A61N 1/37241; A61N 1/3956

USPC ............... 600/506, 508, 513, 536, 546, 547; 128/901
See application file for complete search history.

(56) References Cited

U.S. PATENT DOCUMENTS

| 4,674,518 A | 6/1987 | Salo |
| 4,773,401 A | 9/1988 | Citak et al. |

(Continued)

FOREIGN PATENT DOCUMENTS

| JP | 2004506451 A | 3/2004 |
| JP | 2005532870 A | 11/2005 |

(Continued)

OTHER PUBLICATIONS

"International Application Serial No. PCT/US2009/000095, Invitation to Pay Fees and Partial International Search Rreport mailed May 15, 2009", 7 pgs.

(Continued)

*Primary Examiner* — Devin Henson
(74) *Attorney, Agent, or Firm* — Schwegman Lundberg & Woessner, P.A.

(57) ABSTRACT

An implantable medical device performs impedance measurement and demodulation, such as for obtaining lead impedance measurements, or thoracic impedance measurements, such as for extracting respiration, cardiac stroke, or fluid status information. A 4-point FIR filter demodulator can be used to demodulate a two-phase current excitation waveform. The demodulator can also be used to measure noise for triggering a noise response. Among other things, an increased excitation current level can be used when noise is deemed to be present.

23 Claims, 4 Drawing Sheets

(51) Int. Cl.

| | | |
|---|---|---|
| *A61B 5/029* | (2006.01) | |
| *A61N 1/365* | (2006.01) | |
| *A61N 1/37* | (2006.01) | |
| *A61B 5/04* | (2006.01) | |
| *A61N 1/372* | (2006.01) | |
| *A61N 1/39* | (2006.01) | |
| *A61B 5/046* | (2006.01) | |
| *A61N 1/362* | (2006.01) | |
| *A61B 5/0452* | (2006.01) | |
| *A61B 5/00* | (2006.01) | |
| *A61N 1/08* | (2006.01) | |

(52) U.S. Cl.
CPC .......... *A61N1/36521* (2013.01); *A61B 5/0031* (2013.01); *A61B 5/046* (2013.01); *A61B 5/04017* (2013.01); *A61B 5/0452* (2013.01); *A61B 5/0535* (2013.01); *A61N 1/3622* (2013.01); *A61N 1/3704* (2013.01); *A61N 1/37241* (2013.01); *A61N 1/3956* (2013.01); *A61N 2001/083* (2013.01)

(56) References Cited

U.S. PATENT DOCUMENTS

| | | | |
|---|---|---|---|
| 5,137,019 A | 8/1992 | Pederson et al. | |
| 5,318,597 A | 6/1994 | Hauck et al. | |
| 5,522,860 A | 6/1996 | Molin et al. | |
| 5,817,135 A | 10/1998 | Cooper et al. | |
| 5,824,029 A | 10/1998 | Weijand et al. | |
| 6,044,294 A | 3/2000 | Mortazavi et al. | |
| 6,076,015 A | 6/2000 | Hartley et al. | |
| 6,161,042 A | 12/2000 | Hartley et al. | |
| 6,269,264 B1 | 7/2001 | Weyant et al. | |
| 6,445,951 B1 | 9/2002 | Mouchawar | |
| 6,463,326 B1 | 10/2002 | Hartley et al. | |
| 6,684,101 B2 | 1/2004 | Daum | |
| 6,868,346 B2 | 3/2005 | Larson et al. | |
| 7,092,757 B2 * | 8/2006 | Larson et al. | 607/17 |
| 7,272,442 B2 | 9/2007 | Freeberg | |
| 7,702,389 B2 * | 4/2010 | Czygan et al. | 607/9 |
| 2003/0105499 A1 | 6/2003 | Hartley et al. | |
| 2005/0080460 A1 * | 4/2005 | Wang et al. | 607/17 |
| 2007/0135726 A1 | 6/2007 | Ye et al. | |
| 2007/0150012 A1 | 6/2007 | Czygan et al. | |

FOREIGN PATENT DOCUMENTS

| | | |
|---|---|---|
| JP | 2007508861 A | 4/2007 |
| WO | WO-99/52591 A1 | 10/1999 |
| WO | WO-00/45890 A1 | 8/2000 |
| WO | WO-03/071945 A1 | 9/2003 |
| WO | WO-2004/007019 A2 | 1/2004 |
| WO | WO-2004007019 A2 | 1/2004 |
| WO | WO-2009/089021 A2 | 7/2009 |

OTHER PUBLICATIONS

"International Application Serial No. PCT/US2009/000095, International Search Report mailed Aug. 5, 2009", 6 pgs.

"International Application Serial No. PCT/US2009/000095, Written Opinion mailed Aug. 5, 2009", 10 pgs.

Ye, J., et al., "On-line respiratory artefact removal via adaptive FIR filters in rheopneumographic measurement", *Medical & Biological Engineering & Computing*, 32(6), (Nov. 1994), 620-624.

"Japanese Application Serial No. 2010-542265, Examiners Decision of Final Refusal mailed Mar. 25, 2014", With English Translation, 7 pgs.

"Japanese Application Serial No. 2010-542265, Office Action mailed May 7, 2013", With English Translation, 6 pgs.

"Japanese Application Serial No. 2010-542265, Office Action mailed Jul. 17, 2012", With English Translation, 13 pgs.

"Japanese Application Serial No. 2010-542265, Response filed Oct. 17, 2012 to Office Action mailed Jul. 17, 2012", With English Translation, 10 pgs.

* cited by examiner

IMPEDANCE MEASUREMENT AND DEMODULATION USING IMPLANTABLE DEVICE

CLAIM OF PRIORITY

This non-provisional application claims the benefit of priority under 35 U.S.C. §119(e) to U.S. Provisional Patent Application Ser. No. 61/010,426, filed Jan. 8, 2008, the specification of which is herein incorporated by reference in its entirety.

TECHNICAL FIELD

This document pertains generally to implantable medical devices, and more particularly, but not by way of limitation, to impedance measurement and demodulation using an implantable device.

BACKGROUND

Implantable medical devices (IMDs) include implantable cardiac function management devices, such as, for example, implantable pacers, implantable cardioverters, implantable defibrillators, implantable cardiac resynchronization devices, or any other implantable device for monitoring or influencing cardiac function.

Certain IMDs perform impedance measurements. For example, certain IMDs can measure a "lead impedance," such as exhibited by implanted electrodes located in association with the subject's tissue. Such electrodes may be located on an intravascular leadwire, for example, on a housing of an electronics unit, or elsewhere.

In other examples, certain IMDs can measure a time varying impedance that represents a physiological signal of interest. One example would be an intracardiac impedance, such as between two electrodes located within a heart. Such information can be used to determine a cardiac stroke volume, a pre-ejection interval, or other measurable physiological parameter of interest. This, in turn, can be used to determine or control a therapy, such as a pacing rate, for example. Another example of an impedance-derived time-varying physiological signal of interest would be a thoracic impedance signal observed across at least a portion of a subject's thorax. Physiological information provided by a thoracic impedance signal can include, for example, a cardiac stroke component, which modulates the thoracic impedance signal according to heart contractions, a respiration component, which modulates the thoracic impedance signal according to the subject's breathing, or fluid status information, which modulates the thoracic impedance signal according to pulmonary edema or other changes in the subject's thoracic fluid status.

OVERVIEW

An implantable medical device performs impedance measurement and demodulation, such as for obtaining lead impedance measurements, or thoracic impedance measurements, such as for extracting respiration, cardiac stroke, or fluid status information. A 4-point FIR filter demodulator can be used to demodulate a two-phase current excitation waveform, thus saving current and increasing implanted device longevity. The demodulator can also be used to measure noise for triggering a noise response. Among other things, an increased excitation current level can be used when noise is deemed to be present.

Example 1 describes an apparatus. In this example, the apparatus comprises an implantable impedance measurement circuit, configured to be communicatively coupled to a plurality of implantable electrodes. In this example, the impedance measurement circuit can include an exciter circuit configured to apply a test current between at least two of the electrodes, a preamplifier circuit configured to sense a response signal resulting from the test current using the same or different at least two of the electrodes, and a demodulator circuit communicatively coupled to the preamplifier circuit to demodulate the response signal to the test circuit into a measured signal indicative of an impedance measurement. In this example, the impedance measurement circuit can be configured to perform a noise measurement before obtaining the impedance measurement. The impedance measurement circuit can be adjustably controlled, such as by using information about the noise measurement, to obtain the impedance measurement.

In Example 2, the apparatus of Example 1 can optionally be configured such that the impedance measurement circuit is configured to condition whether to obtain the impedance measurement on whether the noise measurement indicates that at least a specified amount of noise is present.

In Example 3, the apparatus of any one or more of Examples 1-2 can optionally be configured such that the impedance measurement circuit is configured to cancel the impedance measurement when the noise measurement indicates that at least a specified amount of noise is present.

In Example 4, the apparatus of any one or more of Examples 1-3 can optionally be configured such that the impedance measurement circuit is configured to proceed with an impedance measurement when the noise measurement indicates that at least a specified amount of noise is present, and to indicate that the impedance measurement was acquired when at least the specified amount of noise is present.

In Example 5, the apparatus of any one or more of Examples 1-4 can optionally be configured such that the impedance measurement circuit is configured to proceed with the impedance measurement when the noise measurement indicates that at least a specified amount of noise is present, and to increase the test current when at least the specified amount of noise is present.

In Example 6, the apparatus of any one or more of Examples 1-5 can optionally be configured such that the impedance measurement circuit is configured to recurrently perform the noise measurement, to track a number of times that at least the specified amount of noise was present, and to activate a noise indicator using the number of times that at least the specified amount of noise was present using activate a noise indicator when the number of times exceeds a threshold number.

In Example 7, the apparatus of any one or more of Examples 1-6 can optionally be configured such that the impedance measurement circuit is configured to inactivate the indication of noise, after the indication of noise was activated, in response to a number of times that at least the specified amount of noise was not present during a number of noise measurements performed after the indication of noise was activated.

In Example 8, the apparatus of any one or more of Examples 1-7 can optionally include a processor, communicatively coupled to the impedance measuring circuit, the processor configured to extract from the demodulated response signal at least one of respiration information, minute ventilation, cardiac stroke volume, or thoracic fluid status information.

Example 9 describes an apparatus comprising an implantable impedance measurement circuit, configured to be communicatively coupled to a plurality of implantable electrodes. In this example, the impedance measurement circuit can include an exciter circuit, configured to apply a test current between at least two of the electrodes, a preamplifier circuit, configured to sense the voltage response to the test current, a demodulator circuit, communicatively coupled to the preamplifier circuit, wherein the demodulator circuit includes a four-point finite impulse response (FIR) filter. The impedance measurement circuit is configured to determine an impedance measurement between the electrodes using the demodulated sensed voltage response, wherein the exciter circuit is configured to apply a two-phase test current, and wherein the demodulator circuit is configured to demodulate the sensed voltage response to the two-phase test current using the four-point FIR filter.

In Example 10, the apparatus of Example 9 can optionally be configured such that the four-point FIR filter is capable of being represented by a z-domain transfer function of $H(z)=(+a\cdot z^{-4}-b\cdot z^{-3}+b\cdot z^{-2}-a\cdot z^{-1})\div c$, wherein a, b, and c are constant coefficients.

In Example 11, the apparatus of Example 10 can optionally be configured such that $a\neq b$, and $c=2(a+b)$.

Example 12 describes a method. In this example, the method can comprise applying a test current, between at least two implantable electrodes, using an implantable medical device (IMD), wherein applying a test current includes applying a two-phase test current. The method can also comprise sensing a response signal resulting from the test current, demodulating the response signal using a four-point finite impulse response (FIR) filter, wherein demodulating includes demodulating the response signal resulting from the two-phase test current using the four point FIR filter. The method can also comprise determining an impedance using the demodulated response signal.

In Example 13, the method of Example 12 can optionally include pre-sampling a voltage, between electrodes used for sensing the response signal, without applying the test current, determining whether noise is present using the pre-sampled voltage, and controllably adjusting an impedance measurement using information about whether the noise is present.

In Example 14, the method of any one or more of Examples 12-13 can optionally include canceling an impedance measurement when noise is determined to be present.

In Example 15, the method of any one or more of Examples 12-14 can optionally include associating with the impedance measurement an indication of whether noise is determined to have been present with the impedance measurement.

In Example 16, the method of any one or more of Examples 12-15 can optionally include increasing, when noise is determined to be present, the test current used with the impedance measurement.

Example 17 describes a method. In this example, the method can comprise obtaining an impedance measurement, the obtaining comprising applying a test current, between at least two implantable electrodes, using an implantable medical device (IMD), sensing a response signal resulting from the test current, demodulating the response signal, and determining an impedance using the demodulated response signal. In this example, the method can also include determining whether noise is present, and adjustably controlling, using information about whether noise is present, the obtaining the impedance measurement.

In Example 18, the method of Example 17 can optionally be performed such that adjustably controlling includes canceling an impedance measurement when noise is determined to be present.

In Example 19, the method of any one or more of Examples 17-18 can optionally be performed such that adjustably controlling includes associating with the impedance measurement an indication of whether noise is determined to have been present with the impedance measurement.

In Example 20, the method of any one or more of Examples 17-19 can optionally be performed such that adjustably controlling includes increasing, when noise is determined to be present, the test current used with the impedance measurement.

This overview should not be taken as a complete summary of all examples; further examples are described in the below detailed description.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The present inventors have recognized, among other things, a need for improved techniques for measuring impedances, such as by using an implantable medical device.

Figure 1:
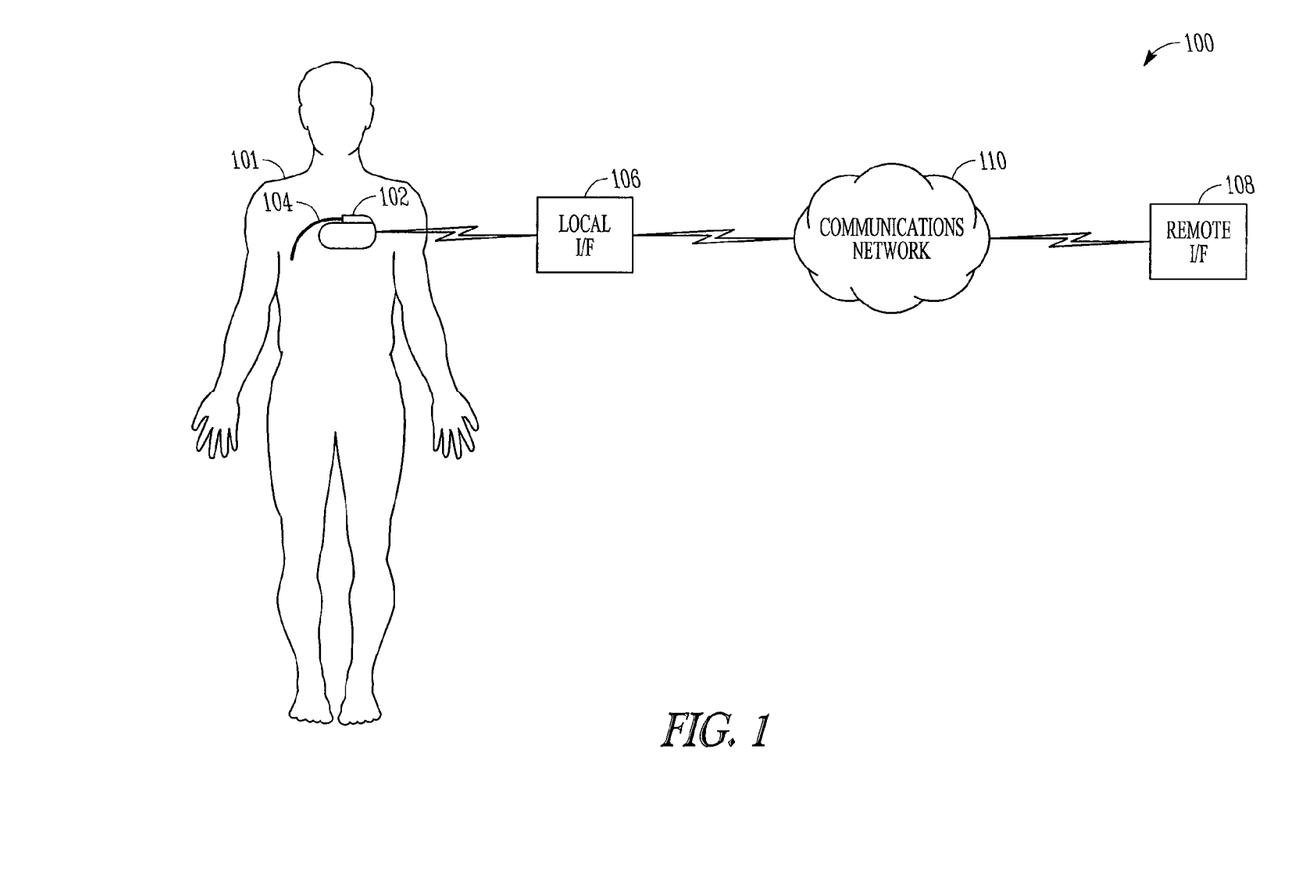
FIG. 1 is schematic diagram illustrating generally an example of a cardiac function management system, such as for use with a human or animal subject.

FIG. 1 is schematic diagram illustrating generally an example of a cardiac function management system 100, such as for use with a human or animal subject 101. In this example, the system 100 includes an implantable cardiac function management device 102, which can include or be coupled to one or more intravascular or other leads 104. The cardiac rhythm management device 102 can include a communication circuit, such as for establishing a bidirectional wireless communication link 105 with an external local interface 106. In certain examples, the external local interface can further bidirectionally communicate with an external remote interface 108, wirelessly or otherwise, such as via a communication network 110.

Figure 2:
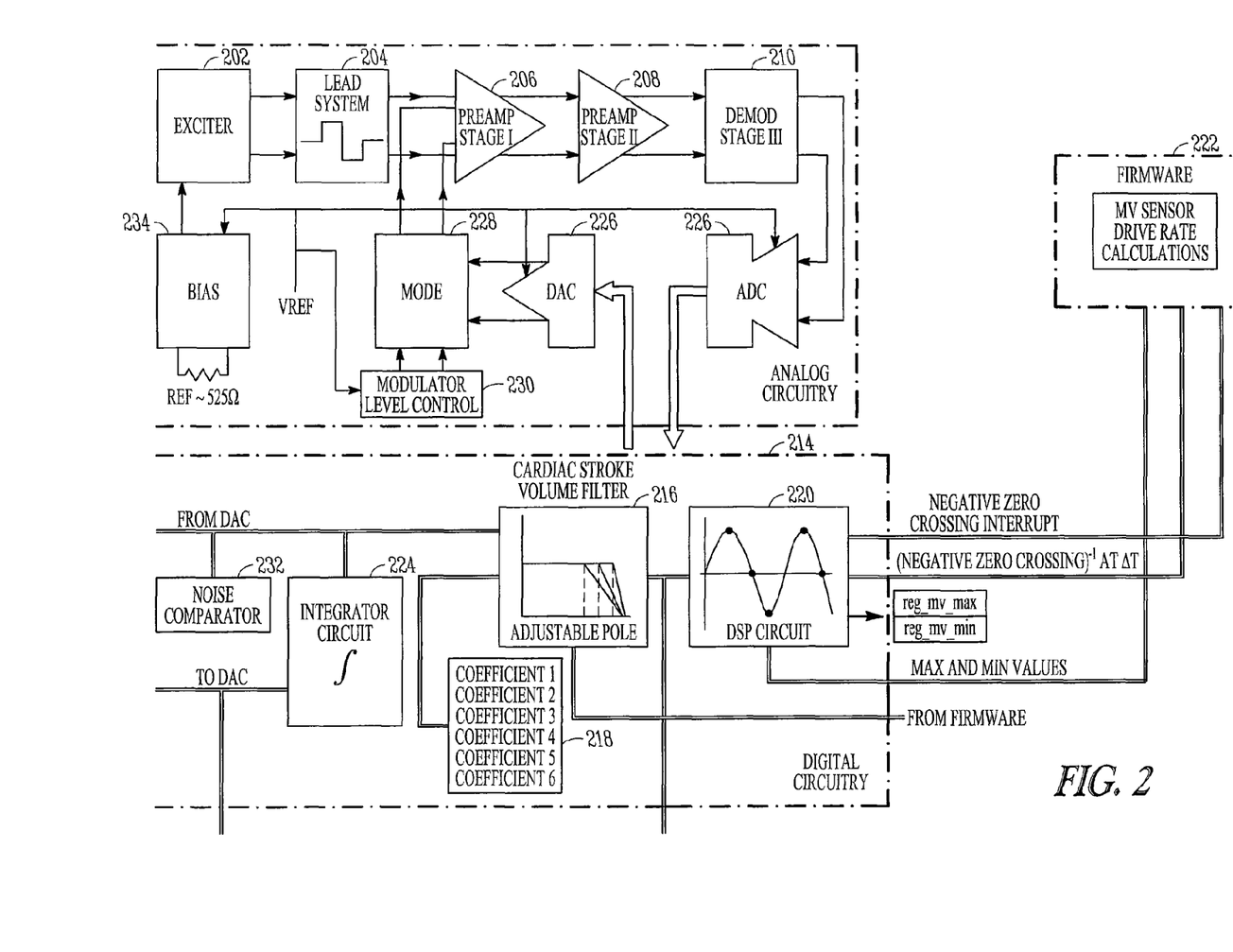
FIG. 2 is a schematic diagram illustrating generally an example of certain portions of the cardiac function device that illustrate an example of impedance measurement.

FIG. 2 is a schematic diagram illustrating generally an example of certain portions of the cardiac function device 102 that illustrate an example of impedance measurement. In certain examples, the impedance measurement can be used for, among other things, deriving a minute ventilation ("MV") physiological signal. The MV signal, in turn, can be used to indicate a patient's metabolic need for cardiac output. Therefore, the MV signal can be used to control a pacing rate delivered to the patient, such as to obtain the cardiac output.

In the example of FIG. 2, an exciter circuit 202 is configured to deliver a test energy (such as a pulsed biphasic or other current waveform) to the subject 101, such as via a lead system 204 or other electrodes to which the exciter circuit 202 is coupled. A response signal is detected (e.g., a response voltage to the delivered test current), and an impedance can be determined (e.g., via Ohm's law). In the example of FIG. 2, a response voltage can be detected by a first stage preamplifier circuit 206, which can sense the response voltage at inputs that are coupled to the lead system 204 or other electrodes (which can be the same electrodes to which the test energy is delivered, or different electrodes, if desired). The first stage preamplifier circuit 206 can output a resulting amplified signal. In the illustrated example, a second stage preamplifier circuit 208 receives the output signal from the first stage preamplifier, and outputs a further amplified signal, which is received at the inputs of a demodulator circuit 210. The demodulator circuit 210 demodulates and further amplifies the amplified response voltage waveform, and outputs a demodulated response signal to an analog-to-digital converter (ADC) 212. The ADC 212 digitizes the demodulated response signal and provides the digitized demodulated response signal (e.g., 12 bits resolution) to a digital circuit 214.

In certain examples, the digital circuit 214 is configured to extract a respiration signal, such as an MV signal, from the digitized demodulated response signal received from the ADC 212. In such an example, the digitized demodulated response signal received from the ADC 212 can be input to a filter circuit 216. The filter circuit 216 can be configured as a lowpass filter to attenuate the cardiac stroke component of the digitized demodulated impedance response signal received from the ADC 212 (and other higher signal frequencies) relative to its higher frequency respiration signal component. In certain examples, the lowpass filter 216 can be configured with an adjustable lowpass filter cutoff frequency, such as by selecting and using stored filter coefficients 218. In certain examples, the adjustable lowpass filter cutoff frequency is dynamically adjusted, for example, as a function of a sensed heart contraction rate. The heart contraction rate can be determined from the cardiac stroke component of the impedance signal, or more likely determined from a separately sensed electrogram signal that is indicative of intrinsic electrical heart activity. As the heart rate increases, the cutoff frequency can be automatically increased as well. Similarly, as the heart rate decreases, the cutoff frequency can be automatically decreased as well.

The respiration component of the thoracic impedance signal, which is output from the lowpass filter circuit 216, is received by a digital signal processor or other digital signal processing (DSP) circuit 220. The DSP circuit 220 can be configured to extract information from the respiration component of the thoracic impedance signal, such as zero-crossings (e.g., negative-going zero-crossings), maximum (peak) values, or minimum (trough) values. From such information, respiration period (or rate) and respiration amplitude can be determined. In certain examples, this information is output to firmware 222, and used to determine a minute ventilation (MV) parameter for providing a physiological sensor indicated metabolic need for cardiac output, which can be used to control ("drive") pacing rate. An illustrative example of using thoracic impedance to derive MV to control pacing rate is described in Hartley et al. U.S. Pat. No. 6,076,015 and Hartley et al. U.S. Pat. No. 6,176,042, each of which is incorporated by reference herein in its entirety, including their disclosure of determining MV from thoracic impedance and using such information to control a pacing rate.

In the example of FIG. 2, the digitized demodulated impedance signal provided by the ADC 212 is also received at an integrator circuit, which provides a resulted integrated feedback signal to a digital-to-analog converter (DAC) circuit 226. The feedback signal is converted to an analog signal by the DAC circuit 226 and provided to a modulator circuit 228, which modulates the feedback signal. The modulated feedback signal is provided to a feedback signal input of the first stage preamplifier circuit 206. In this example, a modulator level control circuit 230 can be coupled to the modulator circuit 228, such as to control over the level of modulation provided to the feedback signal. As described below, the exciter circuit 202 can be programmable to provide different outputs. For example, the exciter circuit 202 can be configured to deliver different test current pulse amplitudes to the lead system 204, for example, switching from 80 microampere current pulses to 320 microampere current pulses when noisy conditions are present, such as can be determined using a noise comparator circuit 232, such as described below. The modulator level control circuit 230 can be configured to provide the appropriate degree of modulation of the feedback signal, such as corresponding to such different settings of the exciter circuit 202. Such different settings of the exciter circuit 202 can be obtained using corresponding different levels of bias currents provided by a bias circuit 234.

Figure 3:
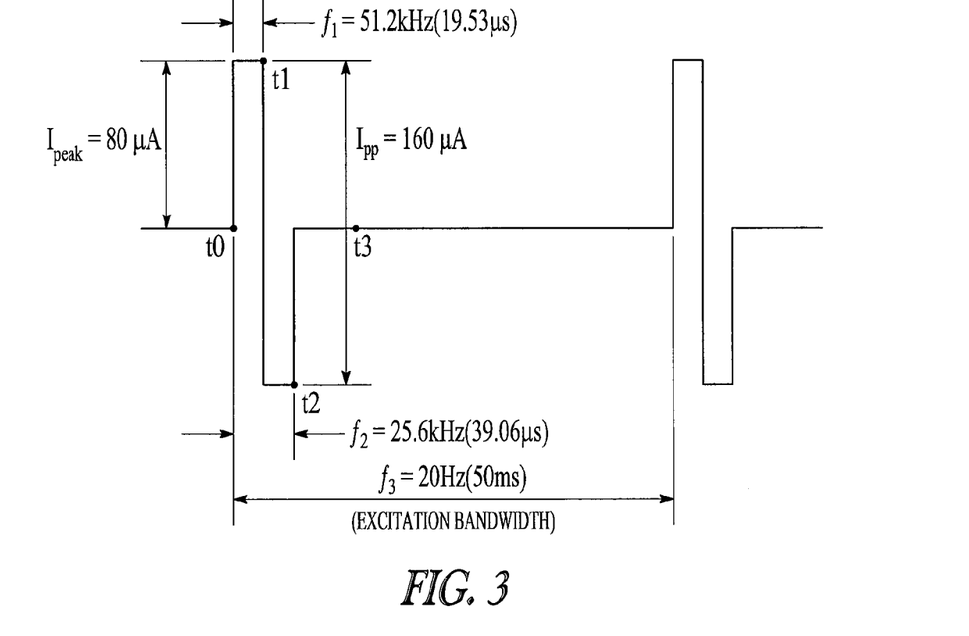
FIG. 3 is an illustrative example of a test current pulse waveform that can be provided by an exciter circuit, such as for obtaining thoracic-impedance derived respiration information.

FIG. 3 is an illustrative example of a test current pulse waveform that can be provided by the exciter circuit 202, such as for obtaining thoracic-impedance derived respiration information, such as to derive an MV parameter for driving pacing rate, in the absence of a detected noise condition. This example provides a two-phase current pulse, which can include a first phase of +80 microamperes for 19.53 microseconds, followed immediately by a second phase of −80 microamperes for 19.53 microseconds. The two-phase current pulse can be repeated at 50 millisecond intervals. When a noise condition is detected, the waveform of FIG. 3 can be automatically altered in response, such as to increase the test current amplitude from +80 microamperes and −80 microamperes to +320 microamperes and −320 microamperes, respectively, for example.

Figure 4:
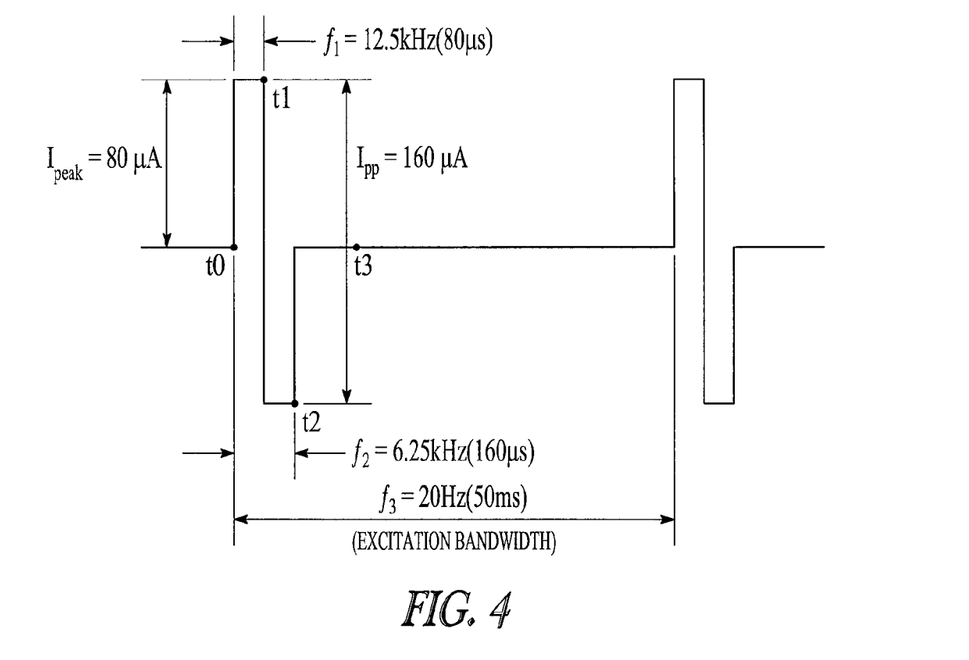
FIG. 4 is an illustrative example of a test current pulse waveform that can be provided by the exciter circuit, such as for obtaining lead impedance information.

FIG. 4 is an illustrative example of a test current pulse waveform that can be provided by the exciter circuit 202, such as for obtaining lead impedance information, in the absence of a detected noise condition. This example provides a two-phase current pulse, which can include a first phase of +80 microamperes for 80 microseconds, followed immediately by a second phase of −80 microamperes for 80 microseconds. The two-phase current pulse can be repeated at 50 millisecond intervals. When a noise condition is detected, the waveform of FIG. 3 can be automatically altered in response, such as to increase the test current amplitude from +80 microamperes and −80 microamperes to +320 microamperes and −320 microamperes, respectively, for example.

The examples of test current pulse waveforms illustrated in FIGS. 3 and 4 produce a voltage response that is indicative of the desired impedance. In certain examples, the lead system 204 can include various electrodes, such as one or more of a right atrial coil (RAC) electrode, a right atrial ring (RAR) electrode, a right atrial tip (RAT) electrode, a right ventricular coil (RVC) electrode, a right ventricular ring (RVR) electrode, a right ventricular tip (RVT) electrode, a left ventricular proximal (LVP) electrode, a left ventricular distal (LVD) electrode, or a housing (CAN) electrode associated with a housing of an electronics unit of the IMD. In a first illustrative example in which thoracic impedance is to be measured, such as for extracting respiration information to derive an MV parameter to control pacing rate, the test current can be driven between the RVC electrode and the CAN electrode, and a resulting voltage response can be measured between the RVT electrode and the CAN electrode. In a second illustrative example in which thoracic impedance is to be measured, such as for extracting respiration information to derive an MV parameter to control pacing rate, the test current can be driven between the RAT electrode and the CAN electrode, and a resulting voltage response can be measured between the RAR electrode and the CAN electrode.

The sensed voltage response to the test current pulse waveforms illustrated in FIGS. 3 and 4 can be demodulated, such as by the demodulator circuit 210. In certain examples, the demodulator circuit 210 includes a 4-point finite impulse response (FIR) filter demodulator. This can be used to sample and demodulate the voltage response at times to (e.g., just before the +80 or +320 microampere first phase current pulse is delivered), $t_1$ (e.g., just before the +80 or +320 microampere second phase current pulse ends), $t_2$ (e.g., just before the −80 or −320 microampere second phase current pulse ends), and $t_3$ (e.g., an additional time period (e.g., equivalent to the duration of the first phase or of the second phase) after the second phase current pulse ends), with respect to the test current waveforms shown in FIGS. 3 and 4. In certain examples, the 4-point FIR filter demodulator includes tap weights of +1, −3, +3, and −1. Such demodulation can be represented by a z-domain transfer function of $H(z) = (+1 \cdot z^{-4} - 3 \cdot z^{-3} + 3 \cdot z^{-2} - 1 \cdot z^{-1}) \div 8$. This particular weighted 4-point FIR filter demodulator provides good performance, including good rejection of intrinsic QRS heart depolarizations, good noise detection capabilities (as discussed below), and good stop band attenuation performance. Moreover, as compared to an approach that uses a similar 4-point demodulator to demodulate a 4-phase test current pulse (e.g., first phase of +80 microamperes, second phase of −80 microamperes, third phase of +80 microamperes, and fourth phase of −80 microamperes), use of the above-described 4-point demodulator in combination with the above-described 2-phase test current pulse provides similar good performance while using only half the current. This is particularly useful in an IMD, which can be powered by a non-rechargeable implanted battery, since such current savings will translate into increased IMD longevity before explant and replacement (with its attendant costs and surgical risks) is needed.

Noise detection can be performed, such as by using the above-described 4-point weighted FIR filter demodulator to demodulate a voltage signal observed in the absence of any test current delivered by the exciter circuit 202. In an illustrative example, such a 4-point demodulated noise sample is automatically triggered, such as at a specified period (e.g., 2.5 milliseconds) before a scheduled measurement (e.g., before a scheduled thoracic impedance measurement, a scheduled lead impedance measurement, or the like). The demodulated signal value is compared to a noise threshold value. If the demodulated signal value exceeds the noise threshold value, then a noise response can be automatically triggered. Multiple different noise threshold values can be used, if desired, such as specific to the particular type of scheduled measurement that is scheduled to follow (e.g., a thoracic impedance measurement, a lead impedance measurement), or even specific to the particular type of information that is desired to be extracted from the scheduled measurement (e.g., for a thoracic impedance measurement, whether respiration information, cardiac stroke information, thoracic fluid status information, or other information is desired).

In certain examples, the triggered noise response includes canceling or ignoring the scheduled impedance measurement, either based upon a single noise detection in excess of the noise threshold value, based upon a specified number (e.g., consecutive, X out of Y, or the like) of noise detections that exceed the noise threshold value.

In certain examples, the triggered noise response includes performing the scheduled impedance measurement, but provides an accompanying indication (e.g., a status bit) indicating that the impedance measurement was acquired under noisy conditions. This can be useful, for example, for a single shot lead impedance measurement that is provided to a processor, such as to monitor IMD operational status.

In certain examples, the triggered noise response includes increasing the energy of the excitation stimulus used to obtain the impedance measurement (for example, bumping the test current pulse amplitude from +/−80 microamperes to +/−320 microamperes in the presence of noisy conditions).

In certain examples, information about the noise detection (e.g., whether noise was detected or how much noise was detected) or about the triggered noise response can be stored in memory in the implantable device or communicated to the local or remote external interface device.

Figure 5:
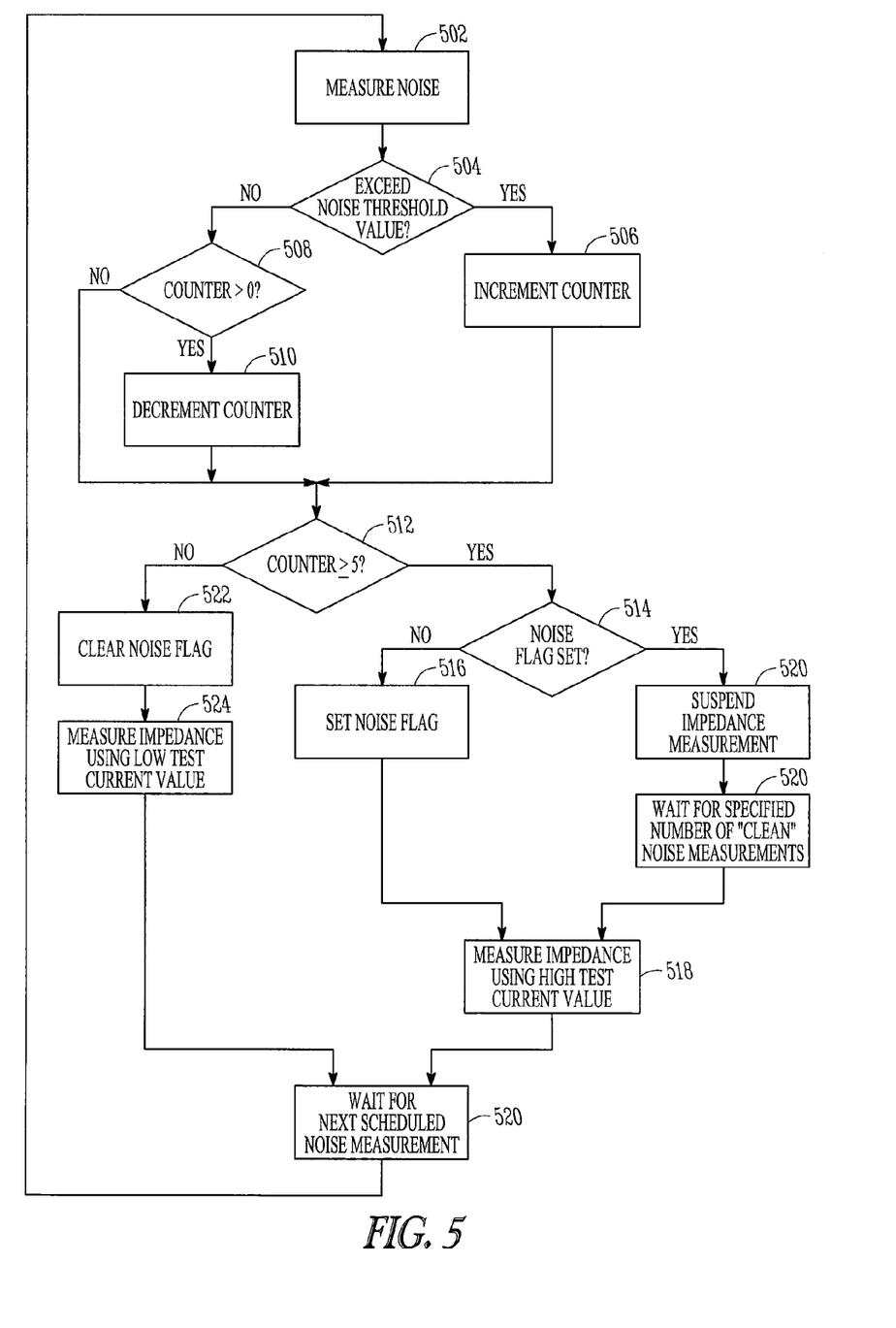
FIG. 5 is a diagram illustrating generally an example of portions of a technique for using noise measurements to automatically trigger a noise response, such as for recurrent thoracic impedance measurements used to obtain a respiration signal.

FIG. 5 is a diagram illustrating generally an example of portions of a technique 500 for using noise measurements to automatically trigger a noise response, such as for recurrent thoracic impedance measurements used to obtain a respiration signal (e.g., for extracting MV and controlling pacing rate, for example). At 502, a scheduled noise measurement is performed. At 504, the noise measurement is compared to a noise threshold value (e.g., equivalent to 250 milliohms, as an illustrative example). If the measured noise exceeds the noise threshold value, then an up/down counter is incremented at 506, otherwise, at 508, the counter is checked to determine whether it is greater than zero. If the counter is greater than zero, then at 510, the counter is decremented, otherwise this step is bypassed and process flow continues to 512. At 512, if the counter value is greater than or equal to a specified value (e.g., five), then at 514, a noise flag is checked. At 514, if the noise flag is not set, then at 516 the noise flag is set before proceeding to 518. At 518, the exciter circuit 202 is programmed to use the higher test current amplitude (e.g., +/−320 microamperes) since noisy conditions are present, and a thoracic impedance measurement is obtained. At 514, if the noise flag is already set, then at 520, thoracic impedance measurements are suspended until, at 522, a specified number (e.g., twelve) of "clean" noise measurements (e.g., noise less than the specified noise threshold value) have been observed. In certain examples, this test for the specified number of clean noise measurements can be imposed using cumulative noise measurements, consecutive noise measurements, or X out of Y noise measurements, if desired. After the condition for clean noise measurements has been met, then process flow continues to 518, where a thoracic impedance measurement is obtained using the higher test current amplitude (e.g., +/−320 microamperes). Then, at 520, the process waits for the next scheduled noise measurement, before process flow returns to 502. At 512, if the counter value is not greater than or equal to the specified value (e.g., five), then at 522 the noise flag is cleared. Then, at 524, a thoracic impedance measurement is obtained using the lower test current amplitude (e.g., +/−80 microamperes). Variations of the example illustrated in FIG. 5 are also possible. For example, instead of using two different current values for measuring thoracic impedance, in certain examples, the particular value of the current used can be made a function of the degree of noise that is observed, e.g., either in terms of the particular measured value of the noise measurement, or in terms of the particular number or frequency of noise measurements exceeding the threshold value.

Although the above description has particularly emphasized an example of using thoracic impedance information for controlling pacing rate based on MV, other useful information (e.g., cardiac stroke information, thoracic fluid status information) can also be obtained from the impedance measurements.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown and described. However, the present inventors also contemplate examples in which only those elements shown and described are provided.

All publications, patents, and patent documents referred to in this document are incorporated by reference herein in their entirety, as though incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An apparatus comprising:
   an implantable impedance measurement circuit, configured to be communicatively coupled to a plurality of implantable electrodes, wherein the impedance measurement circuit includes:
      an exciter circuit, configured to apply a test current between at least two of the electrodes;
      a preamplifier circuit, configured to sense the voltage response to the test current;
      a demodulator circuit, communicatively coupled to the preamplifier circuit,
   wherein the demodulator circuit includes a four-point finite impulse response (FIR) filter;
   and
   wherein the impedance measurement circuit is configured to determine an impedance measurement between the electrodes using the demodulated sensed voltage response, wherein the exciter circuit is configured to apply a two-phase test current that is limited to two-phases per demodulation, and wherein the demodulator circuit is configured to demodulate the sensed voltage response to the two-phase test current using the four-point FIR filter.

2. The apparatus of claim 1, wherein the four-point FIR filter is capable of being represented by a z-domain transfer function of $H(z)=(+a \cdot z^{-4}-b \cdot z^{-3}+b \cdot z^{-2}-a \cdot z^{-1}) \div c$, wherein a, b, and c are constant coefficients.

3. The apparatus of claim 2, wherein $a \neq b$, and wherein $c=2(a+b)$.

4. The apparatus of claim 1, wherein the impedance measurement circuit is configured to perform a noise measurement before obtaining the impedance measurement, and to adjustably control the impedance measurement circuit, using information about the noise measurement, to obtain the impedance measurement.

5. The apparatus of claim 4, wherein the impedance measurement circuit is configured to condition whether to obtain the impedance measurement on whether the noise measurement indicates that at least a specified amount of noise is present.

6. The apparatus of claim 4, wherein the impedance measurement circuit is configured to cancel the impedance measurement when the noise measurement indicates that at least a specified amount of noise is present.

7. The apparatus of claim 4, wherein the impedance measurement circuit is configured to:

proceed with an impedance measurement when the noise measurement indicates that at least a specified amount of noise is present; and indicate that the impedance measurement was acquired when at least the specified amount of noise is present.

8. The apparatus of claim 4, wherein the impedance measurement circuit is configured to:

proceed with the impedance measurement when the noise measurement indicates that at least a specified amount of noise is present; and increase the test current when at least the specified amount of noise is present.

9. The apparatus of claim 4, wherein the impedance measurement circuit is configured to:

recurrently perform the noise measurement;

track a number of times that at least the specified amount of noise was present; and activate a noise indicator using the number of times that at least the specified amount of noise was present when the number of times exceeds a threshold number.

10. The apparatus of claim 9, wherein the impedance measurement circuit is configured to inactivate the indication of noise, after the indication of noise was activated, in response to a number of times that at least the specified amount of noise was not present during a number of noise measurements performed after the indication of noise was activated.

11. A method comprising:

applying a test current, between at least two implantable electrodes, using an implantable medical device (IMD), wherein applying a test current includes applying a two-phase test current that is limited to two-phase per demodulation;

sensing a response signal resulting from the test current;

demodulating the response signal using a four-point finite impulse response (FIR) filter, wherein demodulating includes demodulating the response signal resulting from the two-phase test current using the four point FIR filter; and determining an impedance using the demodulated response signal.

12. The method of claim 11, including:

pre-sampling a voltage, between electrodes used for sensing the response signal, without applying the test current;

determining whether noise is present using the pre-sampled voltage; and controllably adjusting an impedance measurement using information about whether the noise is present.

13. The method of claim 12, including canceling an impedance measurement when noise is determined to be present.

14. The method of claim 12, including associating with the impedance measurement an indication of whether noise is determined to have been present with the impedance measurement.

15. The method of claim 12, including increasing, when noise is determined to be present, the test current used with the impedance measurement.

16. The method of claim 11, comprising:

determining whether noise is present; and controllably adjusting an impedance measurement using information about whether the noise is present.

17. The method of claim 16, wherein controllably adjusting includes canceling an impedance measurement when noise is determined to be present.

18. The method of claim 16, wherein controllably adjusting includes associating with the impedance measurement an indication of whether noise is determined to have been present with the impedance measurement.

19. The method of claim 16, wherein controllably adjusting includes increasing, when noise is determined to be present, the test current used with impedance measurement.

20. An apparatus comprising:

an implantable impedance measurement circuit, configured to be communicatively coupled to a plurality of implantable electrodes, wherein the impedance measurement circuit includes:

an exciter circuit, configured to apply a test current between at least two of the electrodes;

a preamplifier circuit, configured to sense the voltage response to the test current;

a demodulator circuit, communicatively coupled to the preamplifier circuit, wherein the demodulator circuit includes a four-point finite impulse response (FIR) filter having a z-domain transfer function of $H(z)=(+a \cdot z^{-4}-b \cdot z^{-3}+b \cdot z^{-2}-a \cdot z^{-1}) \div c$; and wherein the impedance measurement circuit is configured to determine an impedance measurement between the electrodes using the demodulated sensed voltage response, wherein the exciter circuit is configured to apply a two-phase test current that is limited to two-phases per demodulation, and wherein the demodulator circuit is configured to demodulate the sensed voltage response to the two-phase test current using the four-point FIR filter.

21. The apparatus of claim 20, wherein a, b, and c are constant coefficients.

22. The apparatus of claim 21, wherein $a \neq b$, and wherein $c=2(a+b)$.

23. An apparatus comprising:

an implantable impedance measurement circuit, configured to be communicatively coupled to a plurality of implantable electrodes, wherein the impedance measurement circuit includes:

an exciter circuit, configured to apply a test current between at least two of the electrodes;

a preamplifier circuit, configured to sense the voltage response to the test current;

a demodulator circuit, communicatively coupled to the preamplifier circuit, wherein the demodulator circuit includes a four-point finite impulse response (FIR) filter having a z-domain transfer function of $H(z)=(+a \cdot z^{-4}-b \cdot z^{-3}+b \cdot z^{-2}-a \cdot z^{-1}) \div c$, wherein a, b, and c are constant coefficients, wherein $a \neq b$, and wherein $c=2(a+b)$; and wherein the impedance measurement circuit is configured to determine an impedance measurement between the electrodes using the demodulated sensed voltage response, wherein the exciter circuit is configured to apply a two-phase test current that is limited to two-phases per demodulation, and wherein the demodulator circuit is configured to demodulate the sensed voltage response to the two-phase test current using the four-point FIR filter.

* * * * *